(12) United States Patent
Ghosh

(10) Patent No.: US 10,561,847 B2
(45) Date of Patent: Feb. 18, 2020

(54) CAPTURE MANAGEMENT IN LEADLESS CARDIAC PACING DEVICE

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 191 days.

(21) Appl. No.: 15/906,238

(22) Filed: Feb. 27, 2018

(65) Prior Publication Data

US 2019/0262619 A1  Aug. 29, 2019

(51) Int. Cl.
| | |
|---|---|
| *A61N 1/00* | (2006.01) |
| *A61N 1/37* | (2006.01) |
| *A61N 1/02* | (2006.01) |
| *A61N 1/365* | (2006.01) |
| *A61N 1/375* | (2006.01) |
| *A61N 1/372* | (2006.01) |
| *A61B 5/00* | (2006.01) |
| *A61B 5/044* | (2006.01) |
| *A61B 5/0452* | (2006.01) |
| *A61B 5/042* | (2006.01) |

(52) U.S. Cl.
CPC ............ *A61N 1/3712* (2013.01); *A61B 5/044* (2013.01); *A61B 5/686* (2013.01); *A61N 1/025* (2013.01); *A61N 1/36578* (2013.01); *A61N 1/36585* (2013.01); *A61N 1/371* (2013.01); *A61N 1/3756* (2013.01); *A61N 1/37235* (2013.01); *A61N 1/37512* (2017.08); *A61B 5/0422* (2013.01); *A61B 5/0452* (2013.01)

(58) Field of Classification Search
CPC .... A61N 1/3712; A61N 1/371; A61N 1/3756; A61N 1/37235; A61N 1/36578; A61N 1/37512; A61N 1/36585; A61N 1/025; A61B 5/044; A61B 5/686; A61B 5/0422; A61B 5/0452
See application file for complete search history.

(56) References Cited

U.S. PATENT DOCUMENTS

| | | | |
|---|---|---|---|
| 5,117,824 | A | 6/1992 | Keimel et al. |
| 6,512,940 | B1 | 1/2003 | Brabec et al. |
| 6,522,915 | B1 | 2/2003 | Ceballos et al. |
| 6,622,046 | B2 | 9/2003 | Fraley et al. |
| 8,923,963 | B2 | 12/2014 | Bonner et al. |
| 9,789,319 | B2 | 10/2017 | Sambelashvili |
| 9,808,633 | B2 | 11/2017 | Bonner |

*Primary Examiner* — Scott M. Getzow

(57) ABSTRACT

Capture management in a left ventricular leadless pacing device that includes determining an intrinsic P-wave of a sensed cardiac signal, sensing an electromechanical signal from an electromechanical sensor of the pacing device, and determining an intrinsic electromechanical atrioventricular interval of the sensed electromechanical signal in response to the sensed P-wave. Ventricular pacing is delivered via the one or more electrodes of the pacing device, and a ventricular pacing (V-pace) event is determined in response to the delivered ventricular pacing, and a V-pace to electromechanical response interval is determined in response to the V-pace event. A determination as to capture is detected is made in response to the intrinsic electromechanical atrioventricular interval and the V-pace to electromechanical response interval, and a pacing parameter is determined in response to determining whether capture is detected.

23 Claims, 9 Drawing Sheets

CAPTURE MANAGEMENT IN LEADLESS CARDIAC PACING DEVICE

The disclosure herein relates to an implantable leadless cardiac pacing device, and in particular to a method and apparatus for monitoring of capture management in a left ventricular leadless pacing device using an electromechanical response signal.

BACKGROUND

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers causing a depolarization and the resulting atrial chamber contractions. The excitation pulse is further transmitted to and through the ventricles via the atrioventricular (AV) node and a ventricular conduction system causing a depolarization and the resulting ventricular chamber contractions.

Disruption of this natural pacemaker and conduction system as a result of aging or disease can be treated by artificial cardiac pacing. For example, one or more heart chambers may be electrically paced depending on the location and severity of the conduction disorder. Cardiac therapy, such as cardiac resynchronization therapy (CRT), may correct symptoms of electrical dyssynchrony of a patient's heart by providing pacing therapy to one or both ventricles or atria, e.g., by providing pacing to encourage earlier activation of the left or right ventricles. By pacing the ventricles, the ventricles may be controlled such that they contract in synchrony.

Cardiac resynchronization pacing devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. Delivering electrical stimuli that causes the ventricle to respond is commonly referred to as capturing a ventricle.

Current implantable pacemakers and implantable cardioverter defibrillators (ICDs) are available for delivering electrical stimulation therapies to a patient's heart, such as cardiac resynchronization therapy (CRT). Medical device technology advancement has led toward smaller and smaller implantable devices. Recently, this reduction in size has resulted in the introduction of leadless intracardiac pacemakers that can be implanted directly in a heart chamber. Left ventricular capture management is an important feature for CRT since it helps to ensure that the outputs of the pacing parameters maintain consistent left ventricular pacing. While conventional left ventricular capture management in conventional pacemakers and ICDs is based on right ventricular sensing and atrial pacing, such right ventricular sensing and atrial pacing are not available in a leadless pacing device positioned in a left ventricle of a patient's heart.

SUMMARY

A leadless pacing device may include an integrated accelerometer whose signal can be representative of various mechanical events that occur during the contraction/relaxation cycle of a ventricle of the patient's heart. The time-intervals between these various mechanical events are reflective of cardiac mechanical function and may potentially be used as diagnostic metrics for cardiac dyssynchrony. The present disclosure relates to left capture management in a left ventricular leadless pacemaker that includes defining an intrinsic electromechanical atrioventricular (AV) interval (IEMAVI) as the timing interval between an atrial sensing event (sensed by an accelerometer of the leadless acing device or sensed by an extravascular ICD vector) and the mechanical response as measured by the peak of the accelerometer signal corresponding to systole under conditions of stable non-tachy rhythms. Since the largest peak in the accelerometer signal will correspond to the ventricular systole for patients who have intrinsic AV conduction, the IEMAVI may be determined using a window of the accelerometer signal extending from the intrinsic atrial sense event, such as a 450 ms window.

During capture management, ventricular pacing may be delivered by the left ventricular leadless device simultaneously with an atrial sensing event at a given pacing output, and the ventricular pace to electromechanical response interval (Vp-EMI) may be measured in the same way. Left ventricular capture is detected if IEMAVI>Vp-EMI+a constant-time interval. Example values for the constant time interval may be 20 ms, 30 ms, 40 ms, or 50 ms. The capture management routine may start with the highest pacing output parameters and then step down the outputs till lack of capture is detected. In this way the device may determine pacing thresholds and set margins for appropriate pacing outputs (e.g. 1 V above thresholds, etc) for delivering pacing therapy.

In one example, a method of monitoring capture management in a left ventricular leadless pacing device comprises sensing a cardiac signal via one or more electrodes of the pacing device; determining an intrinsic P-wave of the sensed cardiac signal; sensing an electromechanical signal from an electromechanical sensor of the pacing device, such as an accelerometer signal; determining an intrinsic electromechanical atrioventricular interval of the sensed electromechanical signal in response to the sensed intrinsic P-wave; delivering ventricular pacing via the one or more electrodes of the pacing device; determining a ventricular pacing (V-pace) event in response to the delivered ventricular pacing; determining a V-pace to electromechanical response interval in response to the V-pace event; determining whether capture is detected in response to the intrinsic electromechanical atrioventricular interval and the V-pace to electromechanical response interval; and determining a pacing parameter in response to determining whether capture is detected.

In another example, a left ventricular leadless pacing device comprises: one or more electrodes to sense a cardiac signal; an electromechanical sensor, such as an accelerometer, to sense an electromechanical signal, and a processor configured to determine an intrinsic P-wave of the sensed cardiac signal, determine an intrinsic electromechanical atrioventricular interval in response to the sensed intrinsic P-wave, deliver ventricular pacing via the one or more electrodes, determine a ventricular pacing (V-pace) event in response to the delivered ventricular pacing, determine a V-pace to electromechanical response interval in response to the V-pace event, determine whether capture is detected in response to the intrinsic electromechanical atrioventricular interval and the V-pace to electromechanical response interval, and determine a pacing parameter in response to determining whether capture is detected.

In another example, a non-transitory computer readable medium storing instructions which cause a left ventricular leadless pacing device to perform a method that comprises: sensing a cardiac signal via one or more electrodes of the pacing device; determining an intrinsic P-wave of the sensed cardiac signal; sensing an electromechanical signal from an electromechanical sensor of the pacing device, such as an accelerometer; determining an intrinsic electromechanical atrioventricular interval of the sensed electromechanical signal in response to the sensed intrinsic P-wave; delivering ventricular pacing via the one or more electrodes of the pacing device; determining a ventricular pacing (V-pace) event in response to the delivered ventricular pacing; determining a V-pace to electromechanical response interval in response to the V-pace event; determining whether capture is detected in response to the intrinsic electromechanical atrioventricular interval and the V-pace to electromechanical response interval; and determining a pacing parameter in response to determining whether capture is detected.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
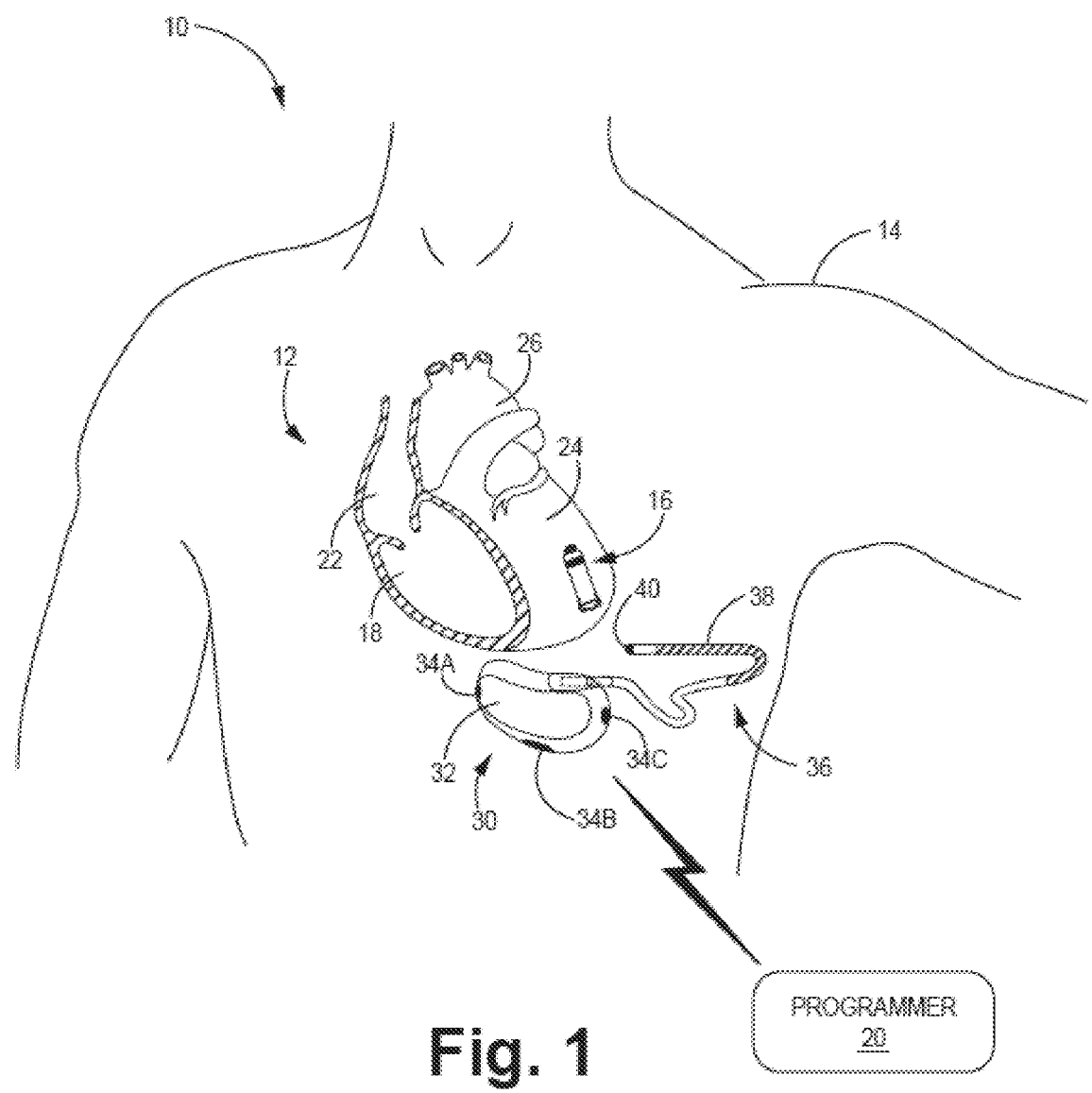
FIG. 1 is a conceptual drawing illustrating an example system that includes a subcutaneous implantable cardioverter defibrillator (SICD) implanted exterior to the rib cage of a patient and a leadless pacing device (LPD) implanted within a cardiac chamber of the patient.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-9. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary system, device and methods described herein relates to left capture management in a left ventricular leadless pacemaker that includes defining an intrinsic electromechanical atrioventricular (AV) interval (IEMAVI) as the timing interval between an atrial sensing event (sensed by an accelerometer of the leadless acing device or sensed by an extravascular ICD vector) and the mechanical response as measured by the peak of the accelerometer signal corresponding to systole under conditions of stable non-tachy rhythms. Since the largest peak in the accelerometer signal will correspond to the ventricular systole for patients who have intrinsic AV conduction, the IEMAVI may be determined using a window of the accelerometer signal extending from the intrinsic atrial sense event, such as a 450 ms window.

During capture management, ventricular pacing may be delivered by the left ventricular leadless device simultaneously with an atrial sensing event at a given pacing output, and the ventricular pace to electromechanical response interval (Vp-EMI) may be measured in the same way. Left ventricular capture is detected if IEMAVI>Vp-EMI+a constant-time interval. Example values for the constant time interval may be 20 ms, 30 ms, 40 ms, or 50 ms. The capture management routine may start with the highest pacing output parameters and then step down the outputs till lack of capture is detected. In this way the device may determine pacing thresholds and set margins for appropriate pacing outputs (e.g. 1 V above thresholds, etc) for delivering pacing therapy.

FIG. 1 is a conceptual drawing illustrating an example system 10 that includes a subcutaneous device (SD) 30 (e.g. SICD, loop recorder (i.e. REVEAL®) etc.) implanted exterior to a rib cage of patient 14 and a leadless pacing device (LPD) 16 implanted within the left ventricle 24 of patient 14. The SD 30 can be implanted external to a rib cage and within the vasculature. Additionally or alternatively, an implantable medical device can be implanted substernally/retrosternally, as described in U.S. Patent Application 61/819,946, entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE" filed May 6, 2013, incorporated by reference in its entirety. In the example of FIG. 1, system 10 includes LPD 16 and SD 30. External programmer 20 may be configured to communicate with one or both of LPD 16 and SD 30. Generally, there are no wires or other direct electrical (e.g., hardwired) connections between SD 30 and LPD 16. In this manner, any communication between SD 30 and LPD 16 may be described as "wireless" communication. Patient 14 is ordinarily, but not necessarily, a human patient.

Exemplary SD 30 includes a housing 32 configured to be subcutaneously implanted outside the rib cage of patient 14. The subcutaneous implantation location may be anterior to the cardiac notch, for example. In addition, housing 32 may carry three subcutaneous electrodes 34A-34C (collectively "electrodes 34"). In other examples, housing 32 may carry fewer or greater than three electrodes. Lead 36 may be configured to couple to housing 32 and extend from housing 32 to a different subcutaneous location within patient 14. For example, lead 36 may be tunneled laterally and posteriorly to the back of patient 14 at a location adjacent to a portion of a latissimus dorsi muscle. Lead 36 may carry electrode coil 38 along a length of lead 36 and sensing electrode 40 at a distal end of lead 36. SD 30 may be configured such that heart 12 may be disposed at least partially between housing 30 and electrode coil 38 of lead 36. In some examples, lead 36 may carry two or more electrode coils 38 and/or two or more sensing electrodes 40.

SD 30 may contain, within housing 32, signal processing and therapy delivery circuitry to detect cardiac conditions (e.g., ventricular dyssnchrony, arrhythmias such as bradycardia and tachycardia conditions etc.) and to communicate with LPD 16 to apply appropriate electrical stimuli (e.g. pacing and/or anti-tachyarrhythmia shock therapy (e.g., defibrillation or cardioversion shocking pulses)) to heart 12. SD 30 also may be configured to apply pacing pulses via one or more electrodes 34. SD 30 may be configured to apply the anti-tachyarrhythmia shock pulses between coil electrode 38 and one or more of electrodes 34 and/or the electrically conductive housing 32 (e.g., an additional can electrode) of SD 30. SD 30 may be configured to communicate with programmer 20 via an RF communication link, inductive coupling, or some other wireless communication protocol.

SD 30 differs from traditionally used ICDs in that housing 32 may be larger in size than the housing of a traditional ICD to accommodate larger capacity batteries, for example. In addition, SD 30 may be implanted subcutaneously whereas a traditional ICD may be implanted under muscle or deeper within patient 14. In other examples, housing 32 may be shaped or sized differently to be implanted subcutaneously instead of under a muscle or within deep tissue. Moreover, SD 30 does not include leads configured to be placed in the bloodstream (e.g., endocardial or epicardial leads). Instead, SD 30 may be configured to carry one or more electrodes (e.g., electrodes 34) on housing 32 together with one or more subcutaneous leads (e.g., lead 36) that carry defibrillation coil electrode 38 and sensing electrode 40. In other examples, lead 36 may include additional electrodes. These subcutaneously implanted electrodes of SD 30 may be used to provide therapies similar to that of traditional ICDs without invasive vascular leads. In other examples, the exact configuration, shape, and size of SD 30 may be varied for different applications or patients. Although SD 30 is generally described as including one or more electrodes, SD 30 may typically include at least two electrodes to deliver an electrical signal (e.g., therapy) and/or provide at least one sensing vector. Other exemplary SDs 30 can be used in combination with LPD 16. For example, SD 30 includes intravenously implanted device (IID), an ICD or a pacemaker or any other suitable device.

System 10 also includes one or more LPDs, such as LPD 16. LPD 16 may be, for example, an implantable leadless pacing device (e.g., a pacemaker, cardioverter, and/or defibrillator) that provides electrical signals to heart 12 via electrodes carried on the housing of LPD 16. In the example of FIG. 1, LPD 16 is implanted within left ventricle 16 of heart 12 to sense electrical activity of heart 12 and/or deliver electrical stimulation, e.g., CRT such as fusion pacing, to heart 12. Fusion pacing involves left ventricle (LV) 24 only pacing with an electrode on the LPD 16 in coordination with the intrinsic right ventricle (RV) activation. Alternatively, fusion pacing can involve pacing the RV with an electrode on the LPD 16 in coordination with the intrinsic LV activation. In this scenario, the LPD 16 is placed within the right ventricle 18.

LPD 16 is schematically shown in FIG. 1 attached to a wall of the left ventricle 24 via one or more fixation elements (e.g. tines, helix etc.) that penetrate the tissue. These fixation elements may secure LPD 16 to the cardiac tissue and retain an electrode (e.g., a cathode or an anode) in contact with the cardiac tissue. LPD 16 may also include one or more motion sensors (e.g., accelerometers) configured to detect and/or confirm cardiac conditions (e.g. ventricular dyssynchrony, tachyarrhythmias etc.) from these mechanical motions of heart 12. Since LPD 16 includes two or more electrodes carried on the exterior housing of LPD 16, no other leads or structures need to reside in other chambers of heart 12. However, in other examples, system 10 may include additional LPDs within respective chambers of heart 12 (e.g., left atrium 26, right atrium 22).

Using the electrodes carried on the housing of LPD 16, LPD 16 may be capable sensing intrinsic electrical signals, e.g., an electrocardiogram (ECG). SD 30 may similarly sense intrinsic electrical signals from the sensing vectors of electrodes 34, 38, and 40. These intrinsic signals may be electrical signals generated by cardiac muscle and indicative of depolarizations and repolarizations of heart 12 at various times during the cardiac cycle. LPD 16 may generate an electrogram from these cardiac signals that may be used by LPD 16 to detect cardiac conditions (e.g. ventricular dyssynchrony, arrhythmias, such as tachyarrhythmias), or identify other cardiac events, e.g., ventricle depolarizations or atrium depolarizations. LPD 16 may also measure impedances of the carried electrodes and/or determine capture thresholds of those electrodes intended to be in contact with cardiac tissue. In addition, LPD 16 may be configured to communicate with external programmer 20. The configurations of electrodes used by LPD 16 for sensing and pacing may be typically considered bipolar but unipolar may also be used.

External programmer 20 may be configured to communicate with one or both of SD 30 and LPD 16. In examples where external programmer 20 only communicates with one of SD 30 and LPD 16, the non-communicative device may receive instructions from or transmit data to the device in communication with programmer 20. In some examples, programmer 20 comprises a handheld computing device, computer workstation, or networked computing device. Programmer 20 may include a user interface that receives input from a user. In other examples, the user may also interact with programmer 20 remotely via a networked computing device. The user may interact with programmer 20 to communicate with LPD 16 and/or SD 30. For example, the user may interact with programmer 20 to send an interrogation request and retrieve therapy delivery data, update therapy parameters that define therapy, manage communication between LPD 16 and/or SD 30, or perform any other activities with respect to LPD 16 and/or SD 30. Although the user is a physician, technician, surgeon, electrophysiologist, or other healthcare professional, the user may be patient 14 in some examples.

Programmer 20 may also allow the user to define how LPD 16 and/or SD 30 senses electrical signals (e.g., ECGs), detects cardiac conditions (e.g. ventricular dyssynchrony, arrhythmias etc.), delivers therapy, and communicates with other devices of system 10. For example, programmer 20 may be used to change detection parameters. In another example, programmer 20 may be used to manage therapy parameters that define therapies such as CRT. Moreover, programmer 20 may be used to alter communication protocols between LPD 16 and SD 30. For example, programmer 20 may instruct LPD 16 and/or SD 30 to switch between one-way and two-way communication and/or change which of LPD 16 and/or SD 30 are tasked with initial detection of a cardiac condition.

Programmer 20 may communicate with LPD 16 and/or SD 30 via wireless communication using any techniques known in the art. Examples of communication techniques may include, for example, radiofrequency (RF) telemetry, but other techniques are also contemplated. In some examples, programmer 20 may include a programming head that may be placed proximate to the patient's body near the LPD 16 and/or SD 30 implant site in order to improve the quality or security of communication between LPD 16 and/or SD 30 and programmer 20.

LPD 16 and SD 30 may engage in communication to facilitate the appropriate detection of ventricular dyssynchrony and/or delivery of CRT. The communication may include one-way communication in which one device is configured to transmit communication messages and the other device is configured to receive those messages. The communication may instead include two-way communication in which each device is configured to transmit and receive communication messages. LPD 16 and SD 30 may be configured to communicate with each other provide alternative electrical stimulation therapies.

Although LPD 16 may at least partially determine whether or not LPD 16 delivers CRT or another therapy to patient 14, LPD 16 may perform one or more functions in response to receiving a request from SD 30 and without any further analysis by LPD 16. In this manner, SD 30 may act as a master device and LPD 16 may act as a slave device. In this configuration, LPD 16 passively senses. Specifically, a VVT mode is employed as a trigger mode to pace in synchrony. In one or more embodiments, the LPD 16 can be configured to actively sense.

Figure 2A:
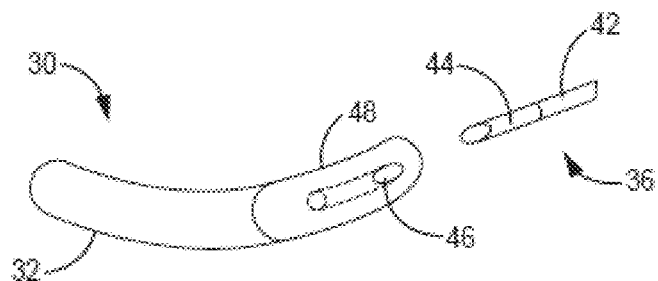
FIGS. 2A and 2B are conceptual drawings illustrating different views of the example SICD of FIG. 1.
Figure 2B:
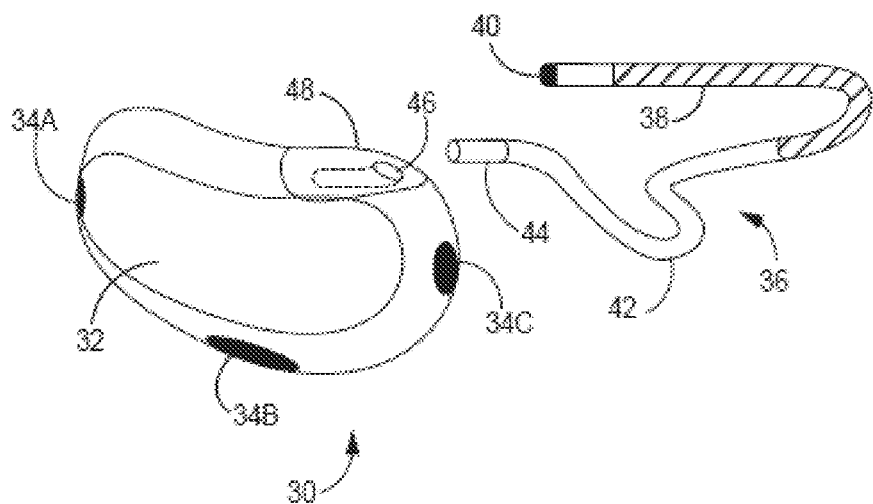

FIGS. 2A and 2B are conceptual drawings illustrating different views of SD 30 of FIG. 1. FIG. 2A is a top view of SD 30, and FIG. 2B is a front view of SD 30. In the example of FIGS. 2A and 2B, housing 32 may be constructed as an ovoid with a substantially kidney-shaped profile. The ovoid shape of housing 32 may promote ease of subcutaneous implantation and may minimize patient discomfort during normal body movement and flexing of the thoracic musculature. In other examples, housing 32 may be constructed with different shapes intended for different implant locations and/or to house different components, subcutaneous leads, or configurations for electrodes 34 FIG. 2B.

Housing 32 may contain the electronic circuitry of SD 30. Header 48 and connector 46 may provide an electrical connection between distal electrode coil 38 and distal sensing electrode 40 of lead 36 and the circuitry within housing 32. Subcutaneous lead 36 may include distal defibrillation coil electrode 38, distal sensing electrode 40, insulated flexible lead body 42 and proximal connector pin 44. Distal sensing electrode 40 may be sized appropriately to match the sensing impedance of electrodes 34A-34C to be used in combination.

In some examples, electrodes 34 are each welded into place on a flattened periphery of housing 32 and are connected to electronic circuitry inside housing 32. Electrodes 34 may be constructed of flat plates, or alternatively, spiral electrodes (as described in U.S. Pat. No. 6,512,940, incorporated herein in its entirety) and mounted in a non-conductive surround shroud (as described in U.S. Pat. Nos. 6,522,915 and 6,622,046, both incorporated herein in their entirety). Electrodes 34 shown in FIG. 2B may be positioned on housing 32 to form orthogonal signal vectors. However, electrodes 34 may be positioned to form any non-orthogonal signal vectors in other examples. In addition, housing 32 may include fewer or greater than three electrodes. Moreover, housing 32 may be configured as an electrically conductive surface and operate as an electrode. Housing 32 may be referred to as a "can electrode" or used as an indifferent electrode. In some examples, housing 32 may be used as an electrode with coil electrode 38 during delivery of (electrical stimuli e.g. pacing pulses, anti-tachyarrhythmia shock).

Figure 3:
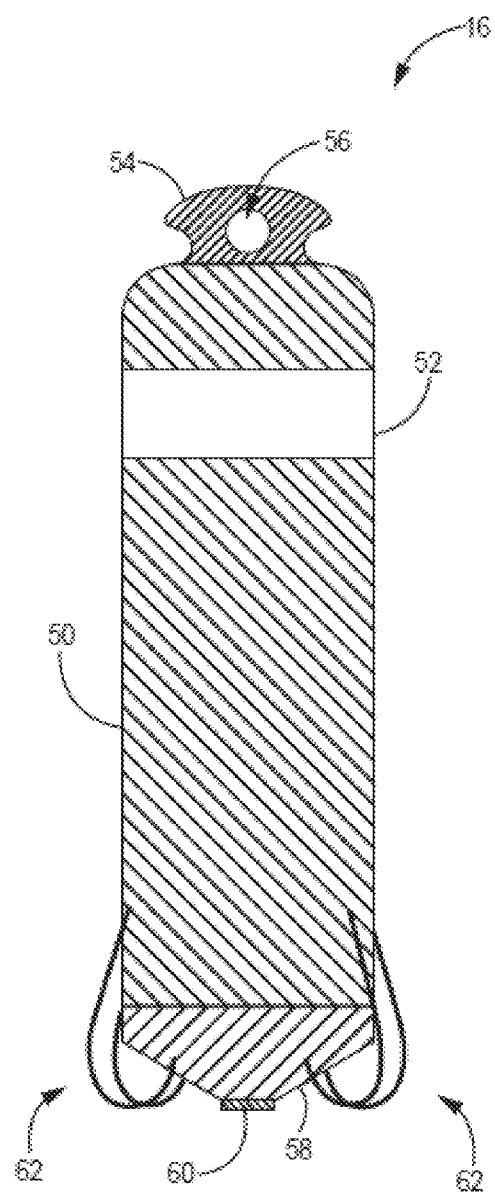
FIG. 3 is a conceptual drawing illustrating the example LPD of FIG. 1.

FIG. 3 is a conceptual drawing illustrating example LPD 16 of FIG. 1. As shown in FIG. 3, LPD 16 includes case 50, cap 58, electrode 60, electrode 52, fixation mechanisms 62, flange 54, and opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16. Although LPD 16 is generally described as including one or more electrodes, LPD 16 may typically include at least two electrodes (e.g., electrodes 52 and 60) to deliver an electrical signal (e.g., therapy such as CRT) and/or provide at least one sensing vector. Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58.

Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering CRT or other appropriate cardiac therapy (ATP, shock etc.). However, electrodes 52 and 60 may be used in any stimulation configuration. In addition, electrodes 52 and 60 may be used to detect intrinsic electrical signals from cardiac muscle. In other examples, LPD 16 may include three or more electrodes, where each electrode may deliver therapy and/or detect intrinsic signals. CRT delivered by LPD 16 may be considered to be "painless" to patient 14 or even undetectable by patient 14 since the electrical stimulation occurs very close to or at cardiac muscle and at relatively low energy levels compared with alternative devices.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 3, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 12 if fixation mechanisms 62 fail. Flange 54 and/or opening 56 may also be used to extract LPD 16 once the LPD needs to be explanted (or removed) from patient 14 if such action is deemed necessary.

In another example, LPD 16 may be configured to be implanted external to heart 12, e.g., near or attached to the epicardium of heart 12. An electrode carried by the housing of the fusion pacing LPD 16 may be placed in contact with the epicardium and/or one or more electrodes placed in contact with the epicardium at locations sufficient to provide therapy (e.g., on external surfaces of the left and/or right ventricles). In any example, SD 30 may communicate with one or more leadless or leaded devices implanted internal or external to heart 12.

Figure 4:
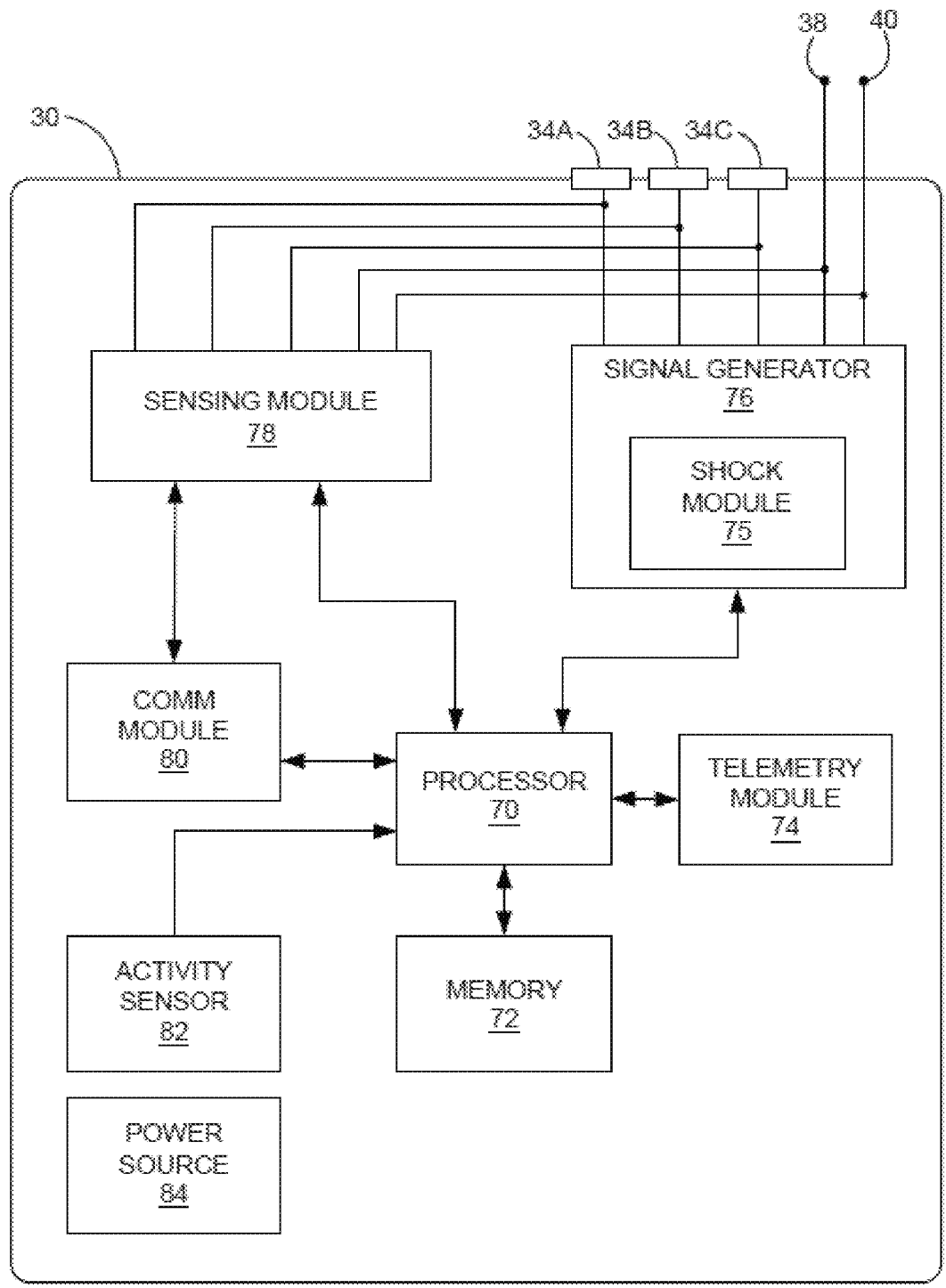
FIG. 4 is a functional block diagram illustrating an example configuration of the SICD of FIG. 1.

FIG. 4 is a functional block diagram illustrating an example configuration of SD 30 of FIG. 1. In the illustrated example, SD 30 includes a processor 70, memory 72, shock module 75, signal generator 76, sensing module 78, telemetry module 74, communication module 80, activity sensor 82, and power source 84. Memory 72 includes computer-readable instructions that, when executed by processor 70, cause SD 30 and processor 70 to perform various functions attributed to SD 30 and processor 70 herein (e.g., detection of ventricular dyssynchrony, communication with LPD 16, and/or delivery of anti-tachyarrhythmia shock therapy, if needed). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Processor 70 controls signal generator 76 to deliver stimulation therapy to heart 12 according to a therapy parameters, which may be stored in memory 72. For example, processor 70 may control signal generator 76 to deliver electrical pulses (e.g., shock pulses) with the amplitudes, pulse widths, frequency, or electrode polarities specified by the therapy parameters. In this manner, signal generator 76 may deliver electrical pulses to heart 12 via electrodes 34, 38, and/or 40. In addition, housing 30 may be configured as an electrode and coupled to signal generator 76 and/or sensing module 78. SD 30 may use any combination of electrodes to deliver anti-tachycardia therapy and/or detect electrical signals from patient 14. However, in general, coil electrode 38 may be used to deliver an anti-tachyarrhythmia shock, if necessary.

Signal generator 76 may also include shock module 75. Shock module 75 may include circuitry and/or capacitors required to deliver an anti-tachyarrhythmia shock. For example, signal generator 76 may charge shock module 75 to prepare for delivering a shock. Shock module 75 may then discharge to enable signal generator 76 to deliver the shock to patient 14 via one or more electrodes. In other examples, shock module 75 may be located within SD 30 but outside of signal generator 76.

Signal generator 76 is electrically coupled to electrodes 34, 38, and 40. In the illustrated example, signal generator 76 is configured to generate and deliver electrical stimuli (e.g. anti-tachyarrhythmia shock therapy) to heart 12. For example, signal generator 76 may, using shock module 75, deliver shocks to heart 12 via a subset of electrodes 34, 38, and 40. In some examples, signal generator 76 may deliver pacing stimulation, and cardioversion or defibrillation shocks in the form of electrical pulses. In other examples, signal generator may deliver one or more of these types of stimulation or shocks in the form of other signals, such as sine waves, square waves, or other substantially continuous time signals.

Signal generator 76 may include a switch module and processor 70 may use the switch module to select, e.g., via a data/address bus, which of the available electrodes are used to deliver shock and/or pacing pulses. The switch module may include a switch array, switch matrix, multiplexer, or any other type of switching device suitable to selectively couple stimulation energy to selected electrodes.

Electrical sensing module 78 may be configured to monitor signals from at least one of electrodes 34, 38, and 40 in order to monitor electrical activity of heart 12, impedance, or other electrical phenomenon. Sensing may be done to determine heart rates or heart rate variability, or to detect arrhythmias (e.g., tachyarrhythmia) or other electrical signals. Sensing module 78 may also include a switch module to select which of the available electrodes are used to sense the heart activity, depending upon which electrode combination, or electrode vector, is used in the current sensing configuration. In examples with several electrodes, processor 70 may select the electrodes that function as sense electrodes, i.e., select the sensing configuration, via the switch module within sensing module 78. Sensing module 78 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 70 may control the functionality of sensing module 78 by providing signals via a data/address bus.

Processor 70 may include a timing and control module, which may be embodied as hardware, firmware, software, or any combination thereof. The timing and control module may comprise a dedicated hardware circuit, such as an ASIC, separate from other processor 70 components, such as a microprocessor, or a software module executed by a component of processor 70, which may be a microprocessor or ASIC. The timing and control module may implement programmable counters. If SD 30 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 70 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 78 for a time interval during and after delivery of electrical stimulation to heart 12. The durations of these intervals may be determined by processor 70 in response to stored data in memory 72. The timing and control module of processor 70 may also determine the amplitude of the cardiac pacing pulses.

Interval counters implemented by the timing and control module of processor 70 may be reset upon sensing of R-waves and P-waves with detection channels of sensing module 78. The value of the count present in the interval counters when reset by sensed R-waves and P-waves may be used by processor 70 to measure the durations of R-R intervals, P-P intervals, P-R intervals and R-P intervals, which are measurements that may be stored in memory 72. In some examples, processor 70 may determine that ventricular dyssynchrony has occurred based on AV interval and P-wave width measurements. Ventricular dyssynchrony is automatically addressed by updating AV delays every minute based on AV interval and P-wave width measurements.

In some examples, communication module 80 may be used to detect communication signals from LPD 16. LPD 16 may not include telemetry circuitry. Instead, LPD 16 may generate electrical signals via one or more electrodes with amplitudes and/or patterns representative of information to be sent to SD 30. The electrical signals may be carried by pacing pulses or separate communication signals configured to be detected by SD 30. In this manner, communication module 80 may be configured to monitor signals sensed by sensing module 78 and determine when a communication message is received from LPD 16.

In other examples, SD 30 may also transmit communication messages to LPD 16 using electrical signals from one or more of electrodes 34, 38, and 40. In this case, communication module 80 may be coupled to signal generator 76 to control the parameters of generated electrical signals or pulses. Alternatively, processor 70 may detect communications via sensing module 78 and/or generate communications for deliver via signal generator 76. Although communication module 80 may be used to communicate using electrical signals via electrodes 34, 38 and 40, communication module 80 may alternatively or in addition use wireless protocols such as RF telemetry to communicate with LPD 16 or other medical devices. In some examples, telemetry module 74 may include this wireless communication functionality.

Memory 72 may be configured to store a variety of operational parameters, therapy parameters, sensed and detected data, and any other information related to the monitoring, therapy and treatment of patient 14. Memory 72 may store, for example, thresholds and parameters indicative of cardiac conditions such as ventricular dyssynchrony and/or therapy parameter values that at least partially define delivered CRT such as fusion pacing. In some examples, memory 72 may also store communications transmitted to and/or received from LPD 16.

Activity sensor 82 may be contained within the housing of SD 30 and include one or more accelerometers or other devices capable of detecting motion and/or position of SD 30. For example, activity sensor 82 may include a 3-axis accelerometer that is configured to detect accelerations in any direction in space. Accelerations detected by activity sensor 82 may be used by processor 70 to identify potential noise in signals detected by sensing module 78 and/or confirm the detection of arrhythmias or other patient conditions.

Telemetry module 74 includes any suitable hardware, firmware, software or any combination thereof for communicating with another device, such as programmer 20 (FIG. 1). As described herein, telemetry module 74 may transmit generated or received arrhythmia data, therapy parameter values, communications between SD 30 and LPD 16, or any other information. For example, telemetry module 74 may transmit information representative of sensed physiological data such as R-R intervals or any other data that may be used by LPD 16 to determine a condition of patient 14. Telemetry module 74 may also be used to receive updated therapy parameters from programmer 20. Under the control of processor 70, telemetry module 74 may receive downlink telemetry from and send uplink telemetry to programmer 20 with the aid of an antenna, which may be internal and/or external. Processor 70 may provide the data to be uplinked to programmer 20 and the control signals for the telemetry circuit within telemetry module 74, e.g., via an address/data bus. In some examples, telemetry module 74 may provide received data to processor 70 via a multiplexer. In some examples, SD 30 may signal programmer 20 to further communicate with and pass the alert through a network such as the Medtronic CareLink® Network developed by Medtronic, Inc., of Minneapolis, Minn., or some other network linking patient 14 to a clinician. SD 30 may spontaneously transmit the diagnostic information to the network or in response to an interrogation request from a user.

Power source 84 may be any type of device that is configured to hold a charge to operate the circuitry of SICD. Power source 84 may be provided as a rechargeable or non-rechargeable battery. In other examples, power source 84 may also incorporate an energy scavenging system that stores electrical energy from movement of SD 30 within patient 14.

There may be numerous variations to the configuration of SD 30, as described herein. In the examples of FIGS. 2A, 2B, and 4, SD 30 may include housing 32 configured to be implanted in patient 14 external to a rib cage of patient 14, one or more electrodes (e.g., electrodes 34, 38, and 40) configured to be disposed external to the rib cage, and shock module 75 configured to at least partially deliver antitachyarrhythmia shock therapy to patient 14 via the one or more electrodes.

SD 30 may also include communication module 80 configured to transmit and/or receive communication messages between LPD 16 configured to be implanted within heart 12 of patient 14 and a sensing module 78 configured to sense an electrical signal from heart 12 of patient 14 via the one or more electrodes. Further, SD 30 may include one or more processors 70 configured to detect a ventricular dyssynchrony within the sensed electrical signal and determine, based on the detected ventricular dyssynchrony, to deliver CRT to patient 14 to treat the detected ventricular dyssynchrony. Processor 70 may also be configured to transmit, via communication module 80 and prior to delivering CRT, a communication message to LPD 16 requesting LPD 16 deliver fusion pacing to heart 12 of patient 14.

Figure 5:
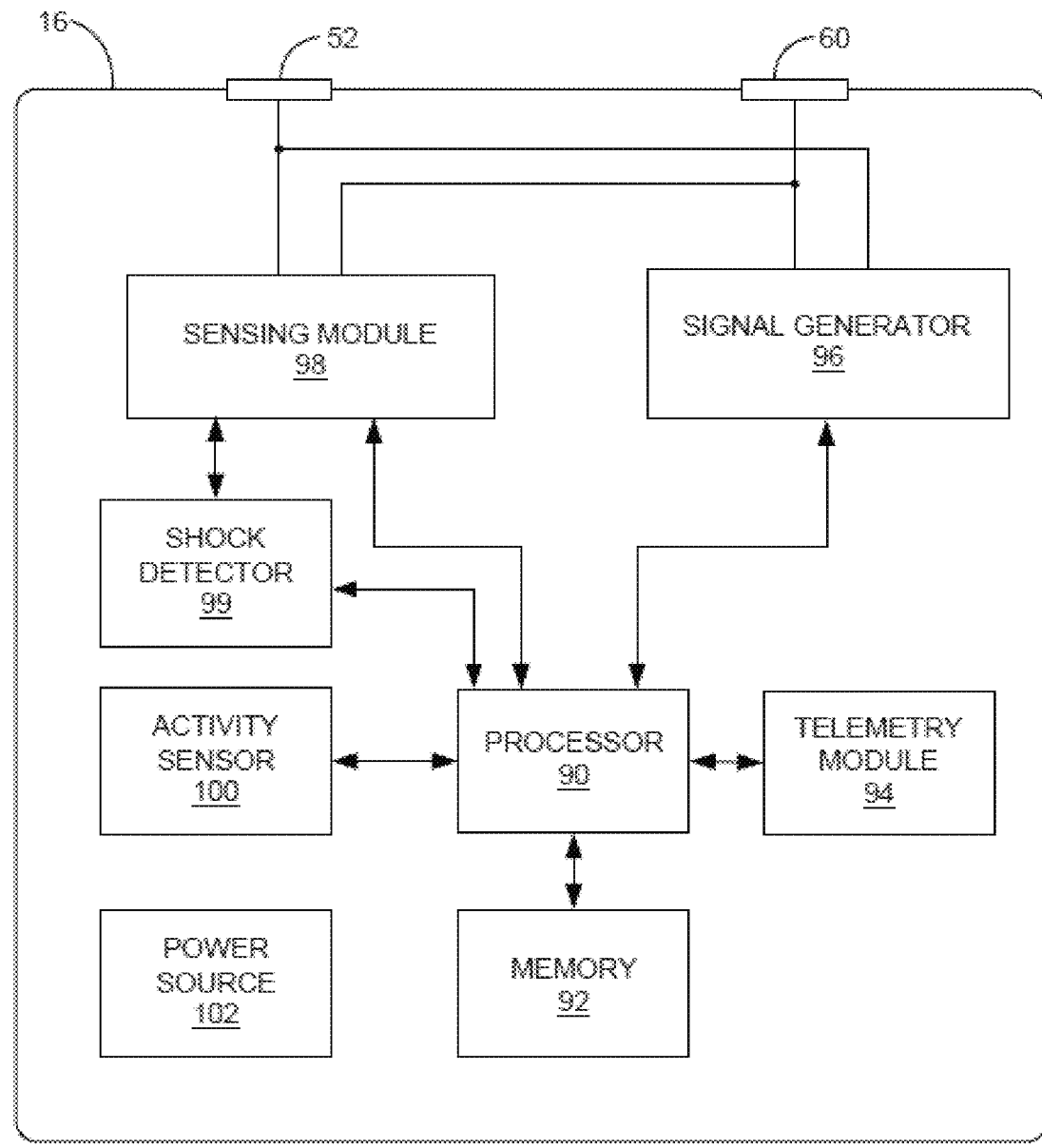
FIG. 5 is a functional block diagram illustrating an example configuration of the LPD of FIG. 1.

FIG. 5 is a functional block diagram illustrating an example configuration of LPD 16 of FIG. 1. In the illustrated example, LPD 16 includes a processor 90, memory 92, signal generator 96, sensing module 98, shock detector 99, activity sensor 100, telemetry module 94, and power source 102. Memory 92 includes computer-readable instructions that, when executed by processor 90, cause LPD 16 and processor 90 to perform various functions attributed to LPD 16 and processor 90 herein (e.g., detecting ventricular dyssnchrony, arrhythmias, communicating with SD 30, and delivering anti-tachycardia pacing and post-shock pacing). Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 90 may include any one or more of a microprocessor, a controller, a digital signal processor (DSP), an application specific integrated circuit (ASIC), a field-programmable gate array (FPGA), or equivalent discrete or analog logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof.

Processor 90 controls signal generator 96 to deliver stimulation therapy to heart 12 according to a therapy parameters, which may be stored in memory 92. For example, processor 90 may control signal generator 96 to deliver electrical pulses with the amplitudes, pulse widths, frequency, or electrode polarities specified by the therapy parameters. In this manner, signal generator 96 may deliver pacing pulses (e.g., fusion pacing) to heart 12 via electrodes 52 and 60. Although LPD 16 may only include two electrodes, e.g., electrodes 52 and 60, LPD 16 may utilize three or more electrodes in other examples. LPD 16 may use any combination of electrodes to deliver therapy and/or detect electrical signals from patient 14.

Signal generator 96 is electrically coupled to electrodes 52 and 60 carried on the housing of LPD 16. In the illustrated example, signal generator 96 is configured to generate and deliver electrical stimulation therapy to heart 12. For example, signal generator 96 may deliver pulses to a portion of cardiac muscle within heart 12 via electrodes 52 and 60. In some examples, signal generator 96 may deliver pacing stimulation in the form of electrical pulses. In other examples, signal generator may deliver one or more of these types of stimulation in the form of other signals, such as sine waves, square waves, or other substantially continuous time signals. Although LPD 16 is generally described has delivering pacing pulses, LPD 16 may deliver cardioversion or defibrillation pulses in other examples.

Fusion pacing may be delivered to patient 14 as defined by a set of parameters. These parameters may include pulse intervals, pulse width, current and/or voltage amplitudes, and durations for each pacing mode.

Signal generator 96 may also include circuitry for measuring the capture threshold of one or both electrodes 52 and 60. The capture threshold may indicate the voltage necessary to induce depolarization of the surrounding cardiac muscle. For example, signal generator 96 may measure the voltage of pacing signals needed to induce synchronized ventricular contractions. In examples in which LPD 16 includes more than two electrodes, signal generator 96 may include a switch module and processor 90 may use the switch module to select, e.g., via a data/address bus, which of the available electrodes are used to deliver pacing pulses. The switch module may include a switch array, switch matrix, multiplexer, or any other type of switching device suitable to selectively couple stimulation energy to selected electrodes.

In the instance that the capture threshold exceeds useable limits, processor 90 may withhold delivery of therapeutic pacing. In addition, processor 90 may transmit communication to SD 30 if pacing cannot be delivered.

Electrical sensing module 98 monitors signals from at least one of electrodes 52 and 60 in order to monitor electrical activity of heart 12, impedance, or other electrical phenomenon. Sensing may be done to determine heart rates or heart rate variability, or to detect ventricular dyssynchrony, arrhythmias (e.g., tachyarrhythmias) or other electrical signals. Sensing module 98 may also include a switch module to select which of the available electrodes (or electrode polarity) are used to sense the heart activity, depending upon which electrode combination, or electrode vector, is used in the current sensing configuration. In examples with several electrodes, processor 90 may select the electrodes that function as sense electrodes, i.e., select the sensing configuration, via the switch module within sensing module 98. Sensing module 98 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 90 may control the functionality of sensing module 98 by providing signals via a data/address bus.

Processor 90 may include a timing and control module, which may be embodied as hardware, firmware, software, or any combination thereof. The timing and control module may comprise a dedicated hardware circuit, such as an ASIC, separate from other processor 90 components, such as a microprocessor, or a software module executed by a component of processor 90, which may be a microprocessor or ASIC. The timing and control module may implement programmable counters. If LPD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing. Example LPDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. patent Ser. No. 13/665,601 to Bonner et al. are both incorporated herein by reference in their entireties.

In addition to detecting and identifying specific types of cardiac rhythms (types of cardiac events), sensing module 98 may also sample the detected intrinsic signals to generate an electrogram or other time-based indication of cardiac events. Processor 90 may also be able to coordinate the delivery of pacing pulses from different LPDs implanted in different chambers of heart 12, such as an LPD implanted in the other ventricle. For example, processor 90 may identify delivered pulses from other LPDs via sensing module 98 and updating pulse timing. In other examples, LPDs may communicate with each other via telemetry module 94 and/or instructions over a carrier wave (such as a stimulation waveform).

Memory 92 may be configured to store a variety of operational parameters, therapy parameters, sensed and detected data, and any other information related to the therapy and treatment of patient 14. In the example of FIG. 5, memory 92 may store sensed ECGs, detected arrhythmias, communications from SD 30, and therapy parameters. In other examples, memory 92 may act as a temporary buffer for storing data until it can be uploaded to SD 30, another implanted device, or programmer 20.

Activity sensor 100 may be contained within the housing of LPD 16 and include one or more accelerometers or other devices capable of detecting motion and/or position of LPD 16. For example, activity sensor 100 may include a 3-axis accelerometer that is configured to detect accelerations in any direction in space. Specifically, the 3-axis accelerator may be used to detect LPD 16 motion that may be indicative of cardiac events and/or noise. For example, processor 16 may monitor the accelerations from activity sensor 100 to confirm or detect arrhythmias. Since LPD 16 may move with a chamber wall of heart 12, the detected changes in acceleration may also be indicative of contractions. Therefore, LPD 16 may be configured to identify heart rates and confirm ventricular dyssynchrony sensed via sensing module 98.

Telemetry module 94 includes any suitable hardware, firmware, software or any combination thereof for communicating with another device, such as programmer 20 or SD 30 (FIG. 1). Under the control of processor 90, telemetry module 94 may receive downlink telemetry from and send uplink telemetry to programmer 20 with the aid of an antenna, which may be internal and/or external. Processor 90 may provide the data to be uplinked to programmer 20 and the control signals for the telemetry circuit within telemetry module 94, e.g., via an address/data bus. In some examples, telemetry module 94 may provide received data to processor 90 via a multiplexer.

In some examples, LPD 16 may signal programmer 20 to further communicate with and pass the alert through a network such as the Medtronic CareLink® Network developed by Medtronic, Inc., of Minneapolis, Minn., or some other network linking patient 14 to a clinician. LPD 16 may spontaneously transmit information to the network or in response to an interrogation request from a user.

In other examples, processor 90 may be configured to transmit information to another device, such as SD 30 using electrodes 52 and 60. For example, processor 90 may control signal generator 96 to generate electrical signals representative of commands such as the detection of ventricular dyssynchrony, confirmation that ventricular dyssynchrony has been detected, a request to monitor electrical signals for ventricular dyssynchrony, or even signals to "wake up" an SICD in a sleep mode. In other examples, processor 90 may cause telemetry module 94 to transmit information representative of sensed physiological data such as R-R intervals or any other data that may be used by SD 30 to determine a condition of patient 14 (e.g., whether or not patient 14 is experiencing ventricular dyssynchrony). The communication may be in the form of dedicated communication signals.

Alternatively, processor 90 may communicate with SD 30 by delivering pacing pulses at specific intervals that would be identifiable by SD 30 as non-physiologic and intended to convey information. In other words, these pulses intended for communication with SD 30. SD 30 may be configured to identify, or distinguish, these pulses from signals indicative of normal or non-normal heart beats, signals indicative of ectopic or non-ectopic heart beats, signals indicative of noise (e.g., skeletal muscle noise), or any other signals indicative of typically physiological or therapeutic electrical signals. The communication pulses may or may not be therapeutic pulses or signals. SD 30 may detect the intervals between these pulses as code for specific messages from LPD 16. For example, the pacing pulses may be varied and/or repeated in certain patterns detectable by SD 30 and still therapeutic. LPD 16 may also be configured to detect such communication messages via electrodes 52 and 60. Processor 90 may monitor sensing module 98 for such communications. Alternatively, LPD 16 may include a communication module, similar to communication module 80 of FIG. 4, to detect any communications received via sensing module 98. In any example, LPD 16 may be configured for one-way communication to or from another device such as SD 30 or two-way communication with another device such as SD 30 using any type of communication protocol.

Power source 102 may be any type of device that is configured to hold a charge to operate the circuitry of LPD 16. Power source 102 may be provided as a rechargeable or non-rechargeable battery. In other example, power source 102 may incorporate an energy scavenging system that stores electrical energy from movement of LPD 16 within patient 14.

There may be numerous variations to the configuration of LPD 16, as described herein. In one example, LPD 16 includes a housing configured to be implanted within heart 12 of patient 14, one or more electrodes (e.g., electrodes 52 and 60) coupled to the housing, fixation mechanism 62 configured to attach the housing to tissue of heart 12, sensing module 98 configured to sense an electrical signal from heart 12 of patient 14 via the one or more electrodes, and signal generator 96 configured to deliver therapy to heart 12 of patient 14 via the one or more electrodes. LPD 16 may also include processor 90 configured to receive a communication message from SD 30 requesting LPD 16 deliver CRT to heart 12, where SD 30 is configured to be implanted exterior to a rib cage of patient 14. Processor 90 may also be configured to determine, based on the sensed electrical signal, whether to deliver CRT to heart 12, and, in response to the determination, command signal generator 96 to deliver the CRT therapy. Processor 90 may also be configured to control signal generator 96 to deliver post-shock pacing to patient 14 in response to shock detector 99 detecting an anti-tachyarrhythmia shock.

Figure 6:
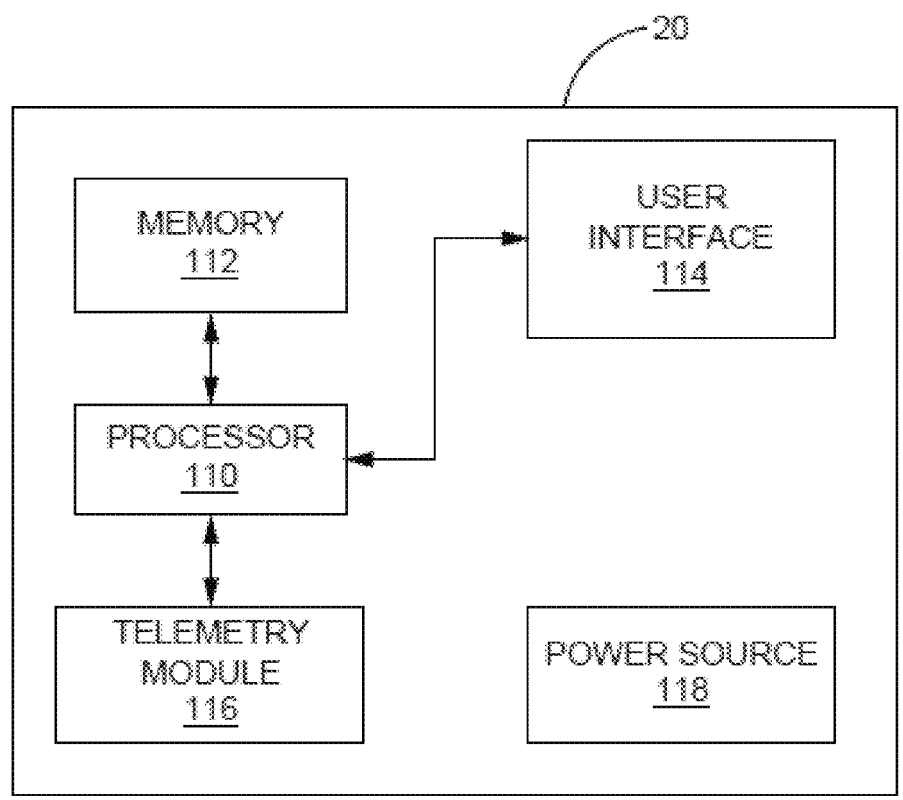
FIG. 6 is a functional block diagram illustrating an example configuration of the programmer of FIG. 1.

FIG. 6 is a functional block diagram illustrating an example configuration of external programmer 20 of FIG. 1. As shown in FIG. 6, programmer 20 may include a processor 110, memory 112, user interface 114, telemetry module 116, and power source 118. Programmer 20 may be a dedicated hardware device with dedicated software for programming of LPD 16 and/or SD 30. Alternatively, programmer 20 may be an off-the-shelf computing device running an application that enables programmer 20 to program LPD 16 and/or SD 30.

A user may use programmer 20 to configure the operational parameters of and retrieve data from LPD 16 and/or SD 30 (FIG. 1). In one example, programmer 20 may communicate directly to both LPD 16 and SD 30. In other examples, programmer may communicate to one of LPD 16 or SD 30, and that device may relay any instructions or information to or from the other device. The clinician may interact with programmer 20 via user interface 114, which may include display to present graphical user interface to a user, and a keypad or another mechanism for receiving input from a user. In addition, the user may receive an alert or notification from SD 30 indicating that a shock has been delivered, any other therapy has been delivered, or any problems or issues related to the treatment of patient 14.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 20 herein, and information used by processor 110 to provide the functionality ascribed to programmer 20 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 20 is used to program therapy for another patient.

Programmer 20 may communicate wirelessly with LPD 16 and/or SD 30, such as using RF communication or proximal inductive interaction. This wireless communication is possible through the use of telemetry module 116, which may be coupled to an internal antenna or an external antenna. An external antenna that is coupled to programmer 20 may correspond to the programming head that may be placed over heart 12 or the location of the intend implant, as described above with reference to FIG. 1. Telemetry module 116 may be similar to telemetry modules 74 and 94 of respective FIGS. 4 and 5.

Telemetry module 116 may also be configured to communicate with another computing device via wireless communication techniques, or direct communication through a wired connection. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. An additional computing device in communication with programmer 20 may be a networked device such as a server capable of processing information retrieved from LPD 16. In other examples, LPD 16 may not use a shock detector to time the beginning or ending of post-shock pacing. Instead, LPD 16 may determine when to deliver post-shock pacing based on a command from SD 30. For example, SD 30 may determine that a shock will be delivered and transmit a shock imminent command to LPD 16. In response to receiving the shock imminent command, LPD 16 may enter a shock state for a predetermined period of time. This predetermined period of time may be stored in memory 92 or sent along with the shock imminent command from SD 30. The predetermined period of time may have a sufficient duration such that any shock would be delivered prior to the predetermined period expiring. In response to the predetermined period elapsing, LPD 16 may exit the shock state and enter a post-shock pacing state in which LPD 16 delivers post-shock pacing and/or first determines whether post-shock pacing is needed.

Figure 7:
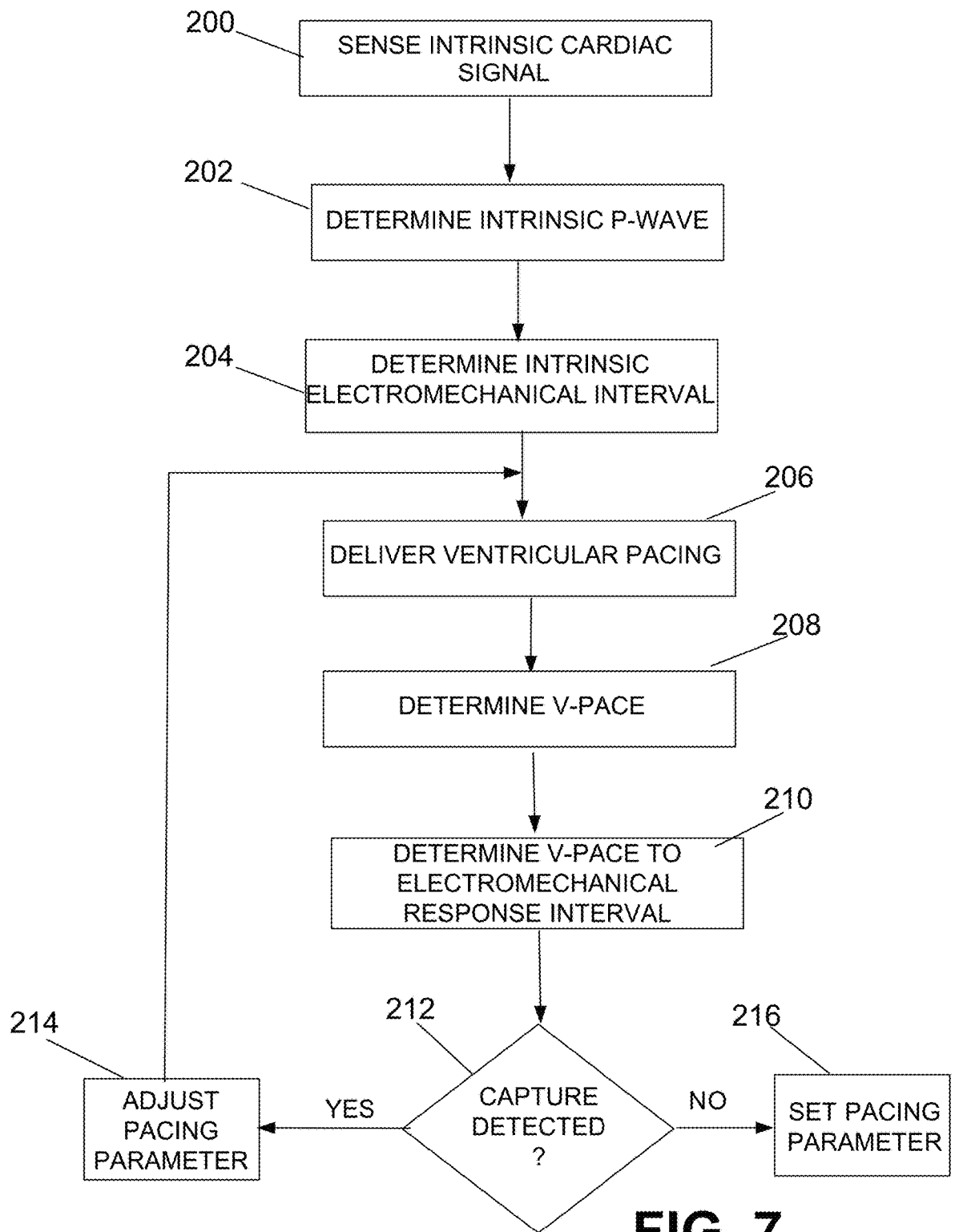
FIG. 7 is a flowchart of a method of monitoring capture management in a left ventricular leadless pacing device according to an example of the present disclosure.

FIG. 7 is a flowchart of a method of monitoring capture management in a left ventricular leadless pacing device according to an example of the present disclosure. As illustrated in FIG. 7, according to one example, during monitoring of capture management in a leadless pacing device, the leadless pacing device senses, via electrodes 52, 60 and sensing module 98, an intrinsic cardiac signal, i.e., corresponding to systole under conditions of stable, non-tachyarrhythmia cardiac rhythm, Block 200. The processor 90 of the pacing device 16 determines the occurrence of an intrinsic P-wave event, Block 202, based either on a signal sensed by the sensor 100 of the leadless pacing device 16, or based on a signal sensed by an extravascular ICD, such as subcutaneous device 30, and received from the extravascular ICD via the telemetry module 94 of the leadless pacing device 16. Based on the determined intrinsic P-wave event, Block 202, the processor 90 of the pacing device 16 determines an intrinsic electromechanical interval associated with the intrinsic P-wave event, Block 204, described below.

In this way, during a capture management procedure, in order to generate pacing parameters that maintain desired consistent left ventricular pacing from a left ventricular leadless pacing device positioned within the left chamber of a patient's heart, the capture management routine begins by the pacing device 16 delivering ventricular pacing therapy via electrodes 52, 60, Block 206. The ventricular pacing therapy may be delivered simultaneously with an atrial sense event at a given pacing output. For example, the ventricular pacing therapy may be delivered using initial predetermined pacing parameters, such as an initial atrial ventricular (AV) interval for example, which controls the timing of ventricular pacing pulses relative to an atrial depolarization, intrinsic or paced. The processor 90 determines timing of a V-pace event, Block 208, and based on the determined V-pace event, Block 208, determines a V-pace to electromechanical response interval, Block 210, described below. A determination is then made, based on the determined intrinsic electromechanical interval, Block 204, and the determined V-pace to electromechanical response interval, Block 210, as to whether capture is detected, Block 212, described below.

If capture is detected, Yes in Block 212, the processor 90 adjusts the pacing parameter, Block 214, and the process, Blocks 206-212, is repeated with the pacing device 16 delivering pacing therapy, Block 206, using the adjusted pacing parameter, Block 214. In one example, the processor 90 may adjust the pacing parameter, Block 214, by reducing the pacing parameter by a predetermined step until lack of capture is detected, Yes in Block 212. For example, the pacing parameter may include a pacing voltage whose initial value may be the maximum pacing voltage output from the device (e.g. 6.0 V) and during capture management routine this parameter may be reduced in steps of 0.5 V.

Once lack of capture is no longer detected, NO in Block 212, the processor 90 stores the pacing parameter, Block 216, in the memory 92 of the pacing device 16 so that pacing therapy may be subsequently delivered using pacing settings associated with the stored pacing parameter.

In one example, based on the pacing parameter setting or settings that were being utilized during delivery of the pacing therapy at the time when capture was no longer detected, No on Block 212, the processor 90 may determine the pacing threshold based on the settings used just prior to when capture was no longer detected, and set margins for desired pacing outputs, such as 1 volt above the threshold, for example, for delivering the pacing therapy.

Figure 8:
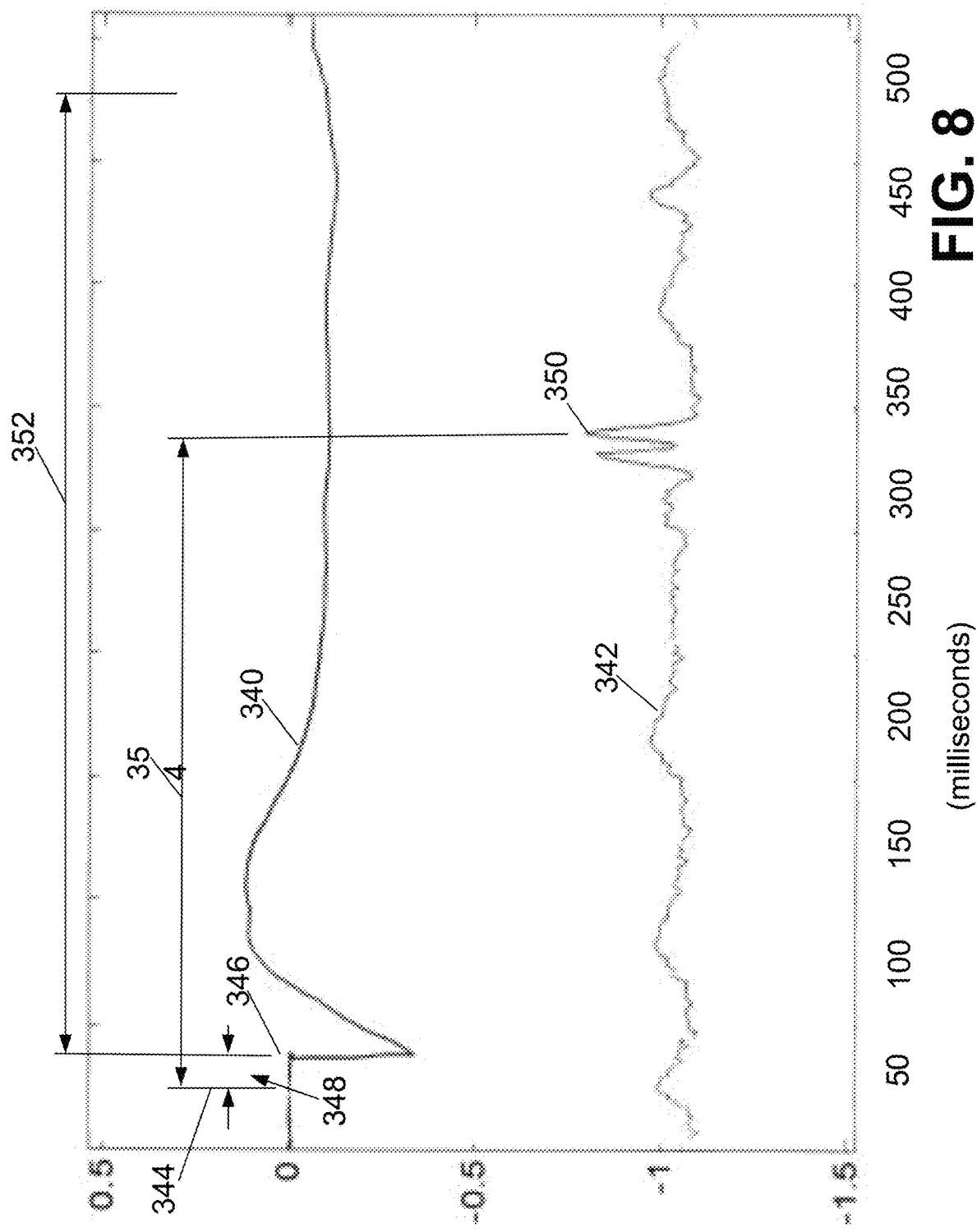
FIG. 8 is a graphical representation of determining of an intrinsic electromechanical interval for a method of monitoring capture management in a left ventricular leadless pacing device according to an example of the present disclosure.

FIG. 8 is a graphical representation of determining of an intrinsic electromechanical interval for a method of monitoring capture management in a left ventricular leadless pacing device according to an example of the present disclosure. As illustrated in FIG. 8, according to one example, in order to determine the intrinsic electromechanical interval, Block 204 of FIG. 7, the processor 90 senses a cardiac signal 340 via electrodes 52, 60 and an electromechanical signal, 342, such as an accelerometer signal, via sensor 100, and determines the occurrence of an intrinsic P-wave 344 based either on the sensed cardiac signal 340 or the sensed electromechanical signal 342.

For example, in order to determine the intrinsic P-wave 344, the processor 90 may determine the occurrence of intrinsic P-wave 344 base on the cardiac signal 340 sensed via electrodes 52, 60 of the device, or based on the cardiac signal 340 being sensed by an extravascular ICD, such as subcutaneous device 30, and received from the extravascular ICD via the telemetry module 94 of the leadless pacing device 16. For example, the processor 90 may determine the occurrence of an intrinsic ventricular event 346 and use an offset interval 348 to identify the intrinsic P-wave 344.

Once the intrinsic P-wave 344 is determined, the processor 90 determines a maximum 350 of the sensed electromechanical signal 342 that occurs within a time window that extends a predetermined time period 352 from the sensed intrinsic P-wave 344. An intrinsic electromechanical interval 354, such as an AV interval for example, is identified as the time period extending from the intrinsic P-wave 344 and the determined maximum 350 of the electromechanical signal.

Figure 9:
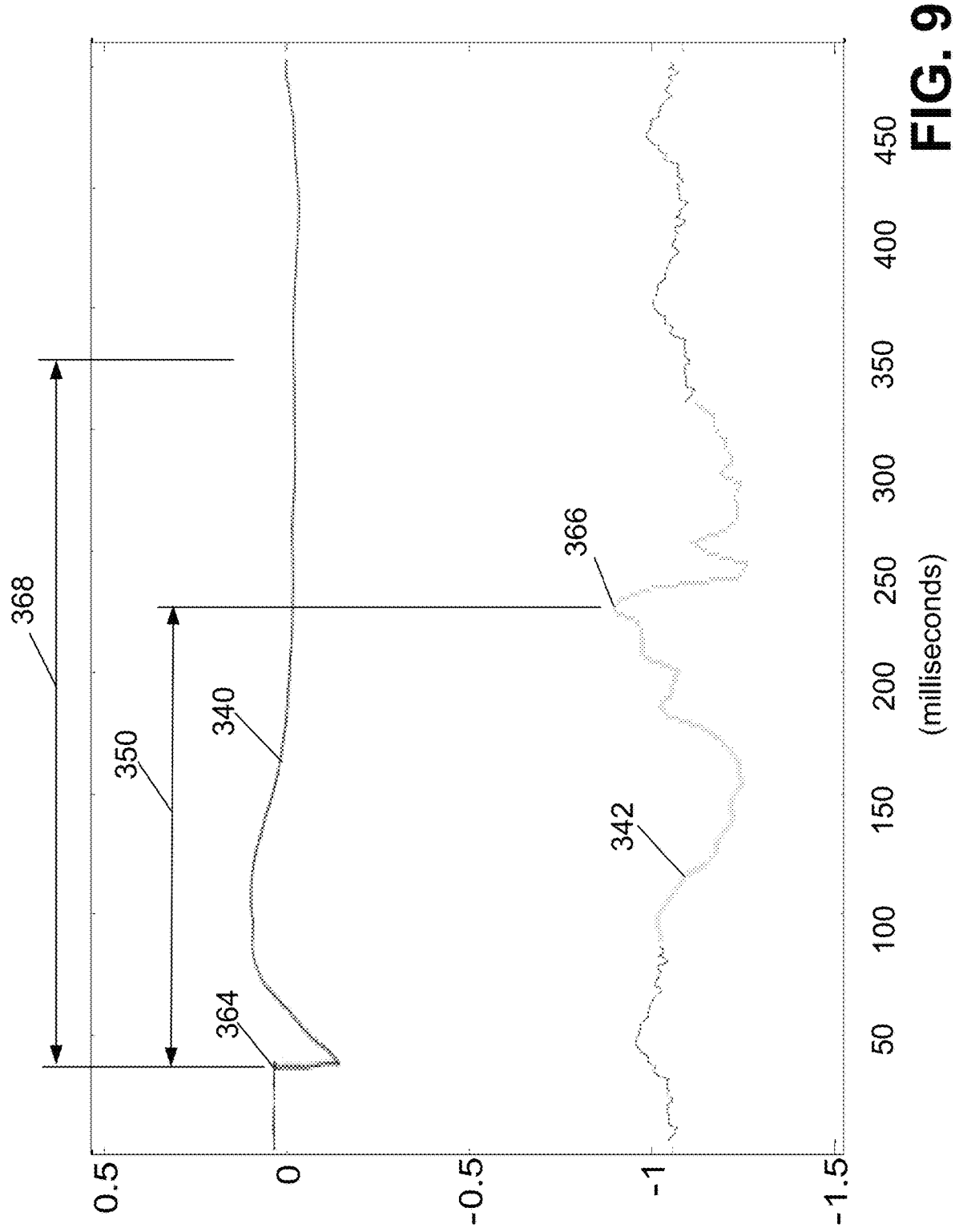
FIG. 9 is a graphical representation of determining of a ventricular-pace event to electromechanical interval for a method of monitoring capture management in a left ventricular leadless pacing device according to an example of the present disclosure.

FIG. 9 is a graphical representation of determining of a ventricular-pace event to electromechanical interval for a method of monitoring capture management in a left ventricular leadless pacing device according to an example of the present disclosure. As illustrated in FIG. 9, according to one example, in order to determine the V-pace to electromechanical response interval, Block 210 of FIG. 7, the processor 90 senses a cardiac signal 340 via electrodes 52, 60 and an electromechanical signal, 342, such as an accelerometer signal, via sensor 100, and determines the occurrence of a V-pace event 364 based either on the sensed cardiac signal 340 sensed directly by the pacing device 16 via electrodes 52, 60, or a sensed cardiac signal being sensed by an extravascular ICD, such as subcutaneous device 30, and received from the extravascular ICD via the telemetry module 94 of the leadless pacing device 16.

Once the V-pace event 364 is determined to occur, the processor 90 determines a maximum 366 of the sensed electromechanical signal 342 that occurs within a time window that extends a predetermined time period 368 from the sensed V-pace event. Exemplary values of this time-window may be 250 ms, 300 ms, 350 ms, 400 ms, 450 ms, 500 ms. In one embodiment this time-window may be adjusted depending on the heart rate or interval between successive cardiac depolarization—the time window may be set to a certain percentage (e.g. 50%) of that interval. For example, if successive atrial sensing events occur at interval of 900 ms, then this window will be 50% of 900=450 ms. A V-pace to electromechanical response interval 370 is identified as the time period that extends from the sensed V-pace event 364 to the determined maximum 366 of the electromechanical signal 342.

In this way, during the determination as to whether capture is detected, Block 212 of FIG. 7, the processor 90 determines whether the intrinsic electromechanical interval 354 is greater than the V-pace to electromechanical response interval 358. If the intrinsic electromechanical interval 354 is greater than the V-pace to electromechanical response interval 370, left ventricular capture is detected, Yes in Block 212. If the intrinsic electromechanical interval 354 is not greater than the V-pace to electromechanical response interval 370, left ventricular capture is not detected, No in Block 212. In one example, a constant time interval associated with the V-pace to electromechanical response interval 370, such as 20 ms, 30 ms, 40 ms or 50 ms for example, may be utilized so that the processor 90 determines whether the intrinsic electromechanical interval 354 is greater than the V-pace to electromechanical response interval 370 plus the constant time interval. If the intrinsic electromechanical interval 354 is greater than the V-pace to electromechanical response interval 370 plus the constant time interval, left ventricular capture is detected, Yes in Block 212. If the intrinsic electromechanical interval 354 is not greater than the V-pace to electromechanical response interval 370 plus the constant time interval, left ventricular capture is not detected, No in Block 212.

The systems and techniques described herein may be generally related to cooperative monitoring of a patient and/or therapy delivery to the patient using multiple implanted devices such as an SD and an LPD. In one example, the SD and LPD may detect the functions of each other and/or communicate to coordinate monitoring and therapy such as CRT. However, the SD and LPD may coordinate other monitoring and therapy features. For example, using the communication techniques described herein, prior to either the SD or LPD delivering therapy, sensed data from both devices may be used to determine if the therapy should be delivered. In some examples, the SD or the LPD may be configured to override the other device in situations in which there is a discrepancy between whether or not physiological condition is occurring. In any case, the SD and LPD may be configured to function together to monitor and/or provide therapy to patient 14.

The techniques described herein may provide for a SD and LPD to operate cooperatively within a patient to monitor the heart for arrhythmias and deliver appropriate therapy to treat any detected arrhythmias. For example, an SD and LPD may detect ventricular dyssynchrony and deliver CRT. Wireless communication between the SD implanted external of the rib cage and one or more LPDs implanted within the heart may provide various ECG or EGM sensing vectors.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

In addition, it should be noted that system 400 may not be limited to treatment of a human patient. In alternative examples, system 400 may be implemented in non-human patients, e.g., primates, canines, equines, pigs, and felines. These other animals may undergo clinical or research therapies that may benefit from the subject matter of this disclosure.

The techniques described in this disclosure, including those attributed to SD 30, LPD 16, programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between SD 30, LPD 16 and/or programmer 20. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Various examples have been described for detecting arrhythmias and delivering anti-tachycardia therapy via a subcutaneous implantable cardioverter defibrillator and/or a leadless pacing device. Any combination of the described operations or functions is contemplated. These and other examples are within the scope of the following claims.

ILLUSTRATIVE EMBODIMENTS

Embodiment 1

A method of monitoring capture management in a left ventricular leadless pacing device, comprising:
sensing a cardiac signal via one or more electrodes of the pacing device;
determining an intrinsic P-wave of the sensed cardiac signal;
sensing an electromechanical signal from an electromechanical sensor of the pacing device;
determining an intrinsic electromechanical atrioventricular interval of the sensed electromechanical signal in response to the sensed intrinsic P-wave;
delivering ventricular pacing via the one or more electrodes of the pacing device;
determining a ventricular pacing (V-pace) event in response to the delivered ventricular pacing;
determining a V-pace to electromechanical response interval in response to the V-pace event;
determining whether capture is detected in response to the intrinsic electromechanical atrioventricular interval and the V-pace to electromechanical response interval; and
determining a pacing parameter in response to determining whether capture is detected.

Embodiment 2

The method of embodiment 1, wherein the electromechanical sensor comprises an accelerometer.

Embodiment 3

The method of any of embodiments 1-2, further comprising:
determining a maximum of the electromechanical signal in response to the intrinsic P-wave; and
determining the intrinsic electromechanical atrioventricular interval in response to the determined maximum of the electromechanical signal.

Embodiment 4

The method of any of embodiments 1-2, further comprising:
determining a maximum of the electromechanical signal in response to in response to the determined V-pace event; and
determining the V-pace to electromechanical response interval in response to the determined maximum of the electromechanical signal.

Embodiment 5

The method of any of embodiments 1-4, further comprising:
determining capture as being detected in response to the intrinsic electromechanical atrioventricular interval being greater than the V-pace to electromechanical response interval; and
determining capture as not being detected in response to the intrinsic electromechanical atrioventricular interval not being greater than the V-pace to electromechanical response interval.

Embodiment 6

The method of any of embodiments 1-4, further comprising:
determining capture as being detected in response to the intrinsic electromechanical atrioventricular interval being greater than a sum of the V-pace to electromechanical response interval and a predetermined time interval; and
determining capture as not being detected in response to the intrinsic electromechanical atrioventricular interval not being greater than the sum of the V-pace to electromechanical response interval and the predetermined time interval.

Embodiment 7

The method of any of embodiments 1-6, further comprising:
  reducing the pacing parameter by a predetermined step in response to capture being detected until lack of capture is detected; and
  determining a pacing threshold based on parameter settings used prior to when capture was no longer detected and setting pacing output margins relative to the threshold for subsequent delivery the ventricular pacing therapy in response to capture not being detected.

Embodiment 8

The method of any of embodiments 1-2, further comprising:
  sensing an electromechanical signal from an electromechanical sensor of the pacing device;
  determining the intrinsic P-wave in response to the cardiac signal;
  determining a first maximum of the electromechanical signal in response to the intrinsic P-wave;
  determining the intrinsic electromechanical atrioventricular interval in response to the determined first maximum of the electromechanical signal;
  determining a second maximum of the electromechanical signal in response to in response to the determined V-pace event; and
  determining the V-pace to electromechanical response interval in response to the determined second maximum of the electromechanical signal.

Embodiment 9

The method of embodiment 8, further comprising:
  determining a first time window extending a predetermined time period from the intrinsic P-wave, wherein the first maximum of the electromechanical signal is determined within the first time window; and
  determining a second time window extending a predetermined time period from the intrinsic V-pace event, wherein the second maximum of the electromechanical signal is determined within the second time window.

Embodiment 10

The method of embodiment 8, further comprising:
  determining capture as being detected in response to the intrinsic electromechanical atrioventricular interval being greater than a sum of the V-pace to electromechanical response interval and a predetermined time interval; and
  determining capture as not being detected in response to the intrinsic electromechanical atrioventricular interval not being greater than the sum of the V-pace to electromechanical response interval and the predetermined time interval.

Embodiment 11

The method of embodiment 8, further comprising:
  reducing the pacing parameter by a predetermined step until lack of capture is detected in response to capture being detected; and
  determining a pacing threshold based on parameter settings used prior to when capture was no longer detected and setting pacing output margins relative to the threshold for subsequent delivery the ventricular pacing therapy in response to capture not being detected.

Embodiment 12

A left ventricular leadless pacing device, comprising:
  one or more electrodes to sense a cardiac signal;
  an electromechanical sensor to sense an electromechanical signal; and
  a processor configured to determine an intrinsic P-wave of the sensed cardiac signal, determine an intrinsic electromechanical atrioventricular interval in response to the sensed intrinsic P-wave, deliver ventricular pacing via the one or more electrodes, determine a ventricular pacing (V-pace) event in response to the delivered ventricular pacing, determine a V-pace to electromechanical response interval in response to the V-pace event, determine whether capture is detected in response to the intrinsic electromechanical atrioventricular interval and the V-pace to electromechanical response interval, and determine a pacing parameter in response to determining whether capture is detected.

Embodiment 13

The device of embodiment 12, wherein the electromechanical sensor comprises an accelerometer.

Embodiment 14

The device of any of embodiments 12-13, wherein the processor is configured determine a maximum of the sensed electromechanical signal in response to the intrinsic P-wave and determine the intrinsic electromechanical atrioventricular interval in response to the determined maximum of the electromechanical signal.

Embodiment 15

The device of any of embodiments 12-13, wherein the processor is further configured to determine a maximum of the electromechanical signal in response to in response to the determined V-pace event and determine the V-pace to electromechanical response interval in response to the determined maximum of the electromechanical signal.

Embodiment 16

The device of any of embodiments 12-16, wherein the processor is configured to determine capture as being detected in response to the intrinsic electromechanical atrioventricular interval being greater than the V-pace to electromechanical response interval, and determine capture as not being detected in response to the intrinsic electromechanical atrioventricular interval not being greater than the V-pace to electromechanical response interval.

Embodiment 17

The device of any of embodiments 12-16, wherein the processor is configured to determine capture as being detected in response to the intrinsic electromechanical atrioventricular interval being greater than a sum of the V-pace to electromechanical response interval and a predetermined time interval, and determine capture as not being detected in response to the intrinsic electromechanical atrioventricular interval not being greater than the sum of the V-pace to electromechanical response interval and the predetermined time interval.

Embodiment 18

The device of any of embodiments 12-16, wherein the processor is configured to reduce the pacing parameter by a predetermined step until lack of capture is detected in response to capture being detected, and determine a pacing threshold based on parameter settings used prior to when capture was no longer detected and setting pacing output margins relative to the threshold for subsequent delivery the ventricular pacing therapy in response to capture not being detected.

Embodiment 19

The device of any of embodiments 12-13, wherein the processor is configured to determine a first maximum of the electromechanical signal in response to the intrinsic P-wave, determine the intrinsic electromechanical atrioventricular interval in response to the determined first maximum of the electromechanical signal, determine a second maximum of the electromechanical signal in response to in response to the determined V-pace event, and determine the V-pace to electromechanical response interval in response to the determined second maximum of the electromechanical signal.

Embodiment 20

The device of any of embodiments 12-19, wherein the processor is configured to determine a first time window extending a predetermined time period from the intrinsic P-wave, determine the first maximum of the electromechanical signal within the first time window, determine a second time window extending a predetermined time period from the intrinsic V-pace event and determine the second maximum of the electromechanical signal within the second time window.

Embodiment 21

The device of any of embodiments 12-20, wherein the processor is configured to determine capture as being detected in response to the intrinsic electromechanical atrioventricular interval being greater than a sum of the V-pace to electromechanical response interval and a predetermined time interval, and determine capture as not being detected in response to the intrinsic electromechanical atrioventricular interval not being greater than the sum of the V-pace to electromechanical response interval and the predetermined time interval.

Embodiment 22

The device of any of embodiments 12-21, wherein the processor is configured to reduce the pacing parameter by a predetermined step in response to capture being detected until lack of capture is detected and determine a pacing threshold based on parameter settings used prior to when capture was no longer detected and setting pacing output margins relative to the threshold for subsequent delivery the ventricular pacing therapy in response to capture not being detected.

Embodiment 23

A non-transitory computer readable medium storing instructions which cause a left ventricular leadless pacing device to perform a method comprising:
  sensing a cardiac signal via one or more electrodes of the pacing device;
  determining an intrinsic P-wave of the sensed cardiac signal;
  sensing an electromechanical signal from an electromechanical sensor of the pacing device;
  determining an intrinsic electromechanical atrioventricular interval of the sensed electromechanical signal in response to the sensed intrinsic P-wave;
  delivering ventricular pacing via the one or more electrodes of the pacing device;
  determining a ventricular pacing (V-pace) event in response to the delivered ventricular pacing;
  determining a V-pace to electromechanical response interval in response to the V-pace event;
  determining whether capture is detected in response to the intrinsic electromechanical atrioventricular interval and the V-pace to electromechanical response interval; and
  determining a pacing parameter in response to determining whether capture is detected.

What is claimed:
1. A method of monitoring capture management in a left ventricular leadless pacing device, comprising:
  sensing a cardiac signal via one or more electrodes of the pacing device;
  determining an intrinsic P-wave of the sensed cardiac signal;
  sensing an electromechanical signal from an electromechanical sensor of the pacing device;
  determining an intrinsic electromechanical atrioventricular interval of the sensed electromechanical signal in response to the sensed intrinsic P-wave;
  delivering ventricular pacing via the one or more electrodes of the pacing device;
  determining a ventricular pacing (V-pace) event in response to the delivered ventricular pacing;
  determining a V-pace to electromechanical response interval in response to the V-pace event;
  determining whether capture is detected in response to the intrinsic electromechanical atrioventricular interval and the V-pace to electromechanical response interval; and
  determining a pacing parameter in response to determining whether capture is detected.

2. The method of claim 1, wherein the electromechanical sensor comprises an accelerometer.

3. The method of claim 2, further comprising:
  determining a maximum of the electromechanical signal in response to the intrinsic P-wave; and
  determining the intrinsic electromechanical atrioventricular interval in response to the determined maximum of the electromechanical signal.

4. The method of claim 2, further comprising:
  determining a maximum of the electromechanical signal in response to in response to the determined V-pace event; and
  determining the V-pace to electromechanical response interval in response to the determined maximum of the electromechanical signal.

5. The method of claim 2, further comprising:
determining capture as being detected in response to the intrinsic electromechanical atrioventricular interval being greater than the V-pace to electromechanical response interval; and
determining capture as not being detected in response to the intrinsic electromechanical atrioventricular interval not being greater than the V-pace to electromechanical response interval.

6. The method of claim 2, further comprising:
determining capture as being detected in response to the intrinsic electromechanical atrioventricular interval being greater than a sum of the V-pace to electromechanical response interval and a predetermined time interval; and
determining capture as not being detected in response to the intrinsic electromechanical atrioventricular interval not being greater than the sum of the V-pace to electromechanical response interval and the predetermined time interval.

7. The method of claim 2, further comprising:
reducing the pacing parameter by a predetermined step in response to capture being detected until lack of capture is detected; and
determining a pacing threshold based on parameter settings used prior to when capture was no longer detected and setting pacing output margins relative to the threshold for subsequent delivery the ventricular pacing therapy in response to capture not being detected.

8. The method of claim 2, further comprising:
sensing an electromechanical signal from an electromechanical sensor of the pacing device;
determining the intrinsic P-wave in response to the cardiac signal;
determining a first maximum of the electromechanical signal in response to the intrinsic P-wave;
determining the intrinsic electromechanical atrioventricular interval in response to the determined first maximum of the electromechanical signal;
determining a second maximum of the electromechanical signal in response to in response to the determined V-pace event; and
determining the V-pace to electromechanical response interval in response to the determined second maximum of the electromechanical signal.

9. The method of claim 8, further comprising:
determining a first time window extending a predetermined time period from the intrinsic P-wave, wherein the first maximum of the electromechanical signal is determined within the first time window; and
determining a second time window extending a predetermined time period from the intrinsic V-pace event, wherein the second maximum of the electromechanical signal is determined within the second time window.

10. The method of claim 8, further comprising:
determining capture as being detected in response to the intrinsic electromechanical atrioventricular interval being greater than a sum of the V-pace to electromechanical response interval and a predetermined time interval; and
determining capture as not being detected in response to the intrinsic electromechanical atrioventricular interval not being greater than the sum of the V-pace to electromechanical response interval and the predetermined time interval.

11. The method of claim 8, further comprising:
reducing the pacing parameter by a predetermined step until lack of capture is detected in response to capture being detected; and
determining a pacing threshold based on parameter settings used prior to when capture was no longer detected and setting pacing output margins relative to the threshold for subsequent delivery the ventricular pacing therapy in response to capture not being detected.

12. A left ventricular leadless pacing device, comprising:
one or more electrodes to sense a cardiac signal;
an electromechanical sensor to sense an electromechanical signal; and
a processor configured to determine an intrinsic P-wave of the sensed cardiac signal, determine an intrinsic electromechanical atrioventricular interval in response to the sensed intrinsic P-wave, deliver ventricular pacing via the one or more electrodes, determine a ventricular pacing (V-pace) event in response to the delivered ventricular pacing, determine a V-pace to electromechanical response interval in response to the V-pace event, determine whether capture is detected in response to the intrinsic electromechanical atrioventricular interval and the V-pace to electromechanical response interval, and determine a pacing parameter in response to determining whether capture is detected.

13. The device of claim 12, wherein the electromechanical sensor comprises an accelerometer.

14. The device of claim 13, wherein the processor is configured determine a maximum of the sensed electromechanical signal in response to the intrinsic P-wave and determine the intrinsic electromechanical atrioventricular interval in response to the determined maximum of the electromechanical signal.

15. The device of claim 13, wherein the processor is further configured to determine a maximum of the electromechanical signal in response to in response to the determined V-pace event and determine the V-pace to electromechanical response interval in response to the determined maximum of the electromechanical signal.

16. The device of claim 13, wherein the processor is configured to determine capture as being detected in response to the intrinsic electromechanical atrioventricular interval being greater than the V-pace to electromechanical response interval, and determine capture as not being detected in response to the intrinsic electromechanical atrioventricular interval not being greater than the V-pace to electromechanical response interval.

17. The device of claim 13, wherein the processor is configured to determine capture as being detected in response to the intrinsic electromechanical atrioventricular interval being greater than a sum of the V-pace to electromechanical response interval and a predetermined time interval, and determine capture as not being detected in response to the intrinsic electromechanical atrioventricular interval not being greater than the sum of the V-pace to electromechanical response interval and the predetermined time interval.

18. The device of claim 13, wherein the processor is configured to reduce the pacing parameter by a predetermined step until lack of capture is detected in response to capture being detected, and determine a pacing threshold based on parameter settings used prior to when capture was no longer detected and setting pacing output margins relative to the threshold for subsequent delivery the ventricular pacing therapy in response to capture not being detected.

19. The device of claim 13, wherein the processor is configured to determine a first maximum of the electromechanical signal in response to the intrinsic P-wave, determine the intrinsic electromechanical atrioventricular interval in response to the determined first maximum of the electromechanical signal, determine a second maximum of the electromechanical signal in response to in response to the determined V-pace event, and determine the V-pace to electromechanical response interval in response to the determined second maximum of the electromechanical signal.

20. The device of claim 18, wherein the processor is configured to determine a first time window extending a predetermined time period from the intrinsic P-wave, determine the first maximum of the electromechanical signal within the first time window, determine a second time window extending a predetermined time period from the intrinsic V-pace event and determine the second maximum of the electromechanical signal within the second time window.

21. The device of claim 19, wherein the processor is configured to determine capture as being detected in response to the intrinsic electromechanical atrioventricular interval being greater than a sum of the V-pace to electromechanical response interval and a predetermined time interval, and determine capture as not being detected in response to the intrinsic electromechanical atrioventricular interval not being greater than the sum of the V-pace to electromechanical response interval and the predetermined time interval.

22. The device of claim 19, wherein the processor is configured to reduce the pacing parameter by a predetermined step in response to capture being detected until lack of capture is detected and determine a pacing threshold based on parameter settings used prior to when capture was no longer detected and setting pacing output margins relative to the threshold for subsequent delivery the ventricular pacing therapy in response to capture not being detected.

23. A non-transitory computer readable medium storing instructions which cause a left ventricular leadless pacing device to perform a method comprising:
sensing a cardiac signal via one or more electrodes of the pacing device;
determining an intrinsic P-wave of the sensed cardiac signal;
sensing an electromechanical signal from an electromechanical sensor of the pacing device;
determining an intrinsic electromechanical atrioventricular interval of the sensed electromechanical signal in response to the sensed intrinsic P-wave;
delivering ventricular pacing via the one or more electrodes of the pacing device;
determining a ventricular pacing (V-pace) event in response to the delivered ventricular pacing;
determining a V-pace to electromechanical response interval in response to the V-pace event;
determining whether capture is detected in response to the intrinsic electromechanical atrioventricular interval and the V-pace to electromechanical response interval; and
determining a pacing parameter in response to determining whether capture is detected.

* * * * *